United States Patent
Bly

(10) Patent No.: US 8,412,350 B2
(45) Date of Patent: *Apr. 2, 2013

(54) NEUROSTIMULATING LEAD HAVING A STENT-LIKE ANCHOR

(75) Inventor: Mark J. Bly, Falcon Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,834

(22) Filed: Mar. 7, 2011

(65) Prior Publication Data

US 2011/0152877 A1  Jun. 23, 2011

Related U.S. Application Data

(63) Continuation of application No. 11/668,834, filed on Jan. 30, 2007, now Pat. No. 7,917,230.

(51) Int. Cl.
*A61N 1/00* (2006.01)

(52) U.S. Cl. ......... 607/116; 607/122; 607/123; 607/125

(58) Field of Classification Search .................. 607/116, 607/122, 123, 125
See application file for complete search history.

(56) References Cited

U.S. PATENT DOCUMENTS

| | | |
|---|---|---|
| 4,365,634 A | 12/1982 | Bare et al. |
| 4,414,986 A | 11/1983 | Dickhudt et al. |
| 4,774,949 A | 10/1988 | Fogarty |
| 4,905,667 A | 3/1990 | Foerster et al. |
| 4,920,979 A | 5/1990 | Bullara |
| 4,944,088 A | 7/1990 | Doan et al. |
| 5,016,808 A | 5/1991 | Heil, Jr. et al. |
| 5,117,828 A | 6/1992 | Metzger et al. |
| 5,170,802 A | 12/1992 | Mehra |
| 5,221,261 A | 6/1993 | Termin et al. |
| 5,265,608 A | 11/1993 | Lee et al. |
| 5,330,515 A | 7/1994 | Rutecki et al. |
| 5,351,394 A | 10/1994 | Weinberg |
| 5,354,318 A | 10/1994 | Raepke |
| 5,378,239 A | 1/1995 | Termin et al. |
| 5,383,922 A | 1/1995 | Zipes et al. |
| 5,387,233 A | 2/1995 | Alferness et al. |

(Continued)

FOREIGN PATENT DOCUMENTS

| | | |
|---|---|---|
| DE | 10103288 | 8/2002 |
| DE | 10103288 A1 | 8/2002 |

(Continued)

OTHER PUBLICATIONS

Goldberger JJ, Kadish AH, Johnson D, Qi X. New Technique for Vagal Nerve Stimulation. J Neurosci Methods. Sep. 15, 1999; 91 (1-2): 109-14.

(Continued)

*Primary Examiner* — Niketa Patel
*Assistant Examiner* — William Levicky
(74) *Attorney, Agent, or Firm* — Faegre Baker Daniels LLP

(57) ABSTRACT

A neurostimulating lead having a stent-like anchor is described. A distal portion of the lead is mounted to an exterior of an expandable, stent-like lead anchor. The stent-like lead anchor is formed from a superelastic material and is adapted to transition from a collapsed configuration to an expanded configuration upon deployment in a vessel. In the expanded configuration, the lead anchor presses the distal portion of the lead against at least one vessel wall of a vessel in which the lead is deployed securing and stabilizing the distal portion of the lead within the vessel.

20 Claims, 8 Drawing Sheets

U.S. PATENT DOCUMENTS

| | | | |
|---|---|---|---|
| 5,411,546 | A | 5/1995 | Bowald et al. |
| 5,423,865 | A | 6/1995 | Bowald et al. |
| 5,476,498 | A | 12/1995 | Ayers |
| 5,496,277 | A | 3/1996 | Termin et al. |
| 5,531,779 | A | 7/1996 | Dahl et al. |
| 5,540,730 | A | 7/1996 | Terry, Jr. et al. |
| 5,639,276 | A | 6/1997 | Weinstock et al. |
| 5,755,714 | A | 5/1998 | Murphy-Chutorian |
| 5,755,761 | A | 5/1998 | Obino |
| 5,766,203 | A | 6/1998 | Imran et al. |
| 5,772,693 | A | 6/1998 | Brownlee |
| 5,792,187 | A | 8/1998 | Adams |
| 5,803,928 | A | 9/1998 | Tockman et al. |
| 5,871,531 | A | 2/1999 | Struble |
| 5,954,761 | A | 9/1999 | Machek et al. |
| 5,997,536 | A | 12/1999 | Osswald et al. |
| 6,006,134 | A | 12/1999 | Hill |
| 6,021,354 | A | 2/2000 | Warman et al. |
| 6,055,456 | A | 4/2000 | Gerber |
| 6,292,695 | B1 * | 9/2001 | Webster et al. .............. 607/14 |
| 6,321,123 | B1 | 11/2001 | Morris et al. |
| 6,363,288 | B1 | 3/2002 | Bush et al. |
| 6,385,492 | B1 | 5/2002 | Ollivier et al. |
| 6,397,109 | B1 | 5/2002 | Cammilli et al. |
| 6,429,217 | B1 | 8/2002 | Puskas |
| 6,442,413 | B1 | 8/2002 | Silver |
| 6,449,507 | B1 | 9/2002 | Hill et al. |
| 6,516,232 | B2 | 2/2003 | Skinner |
| 6,522,926 | B1 | 2/2003 | Kieval et al. |
| 6,564,096 | B2 | 5/2003 | Mest |
| 6,584,362 | B1 | 6/2003 | Scheiner et al. |
| 6,600,956 | B2 | 7/2003 | Maschino et al. |
| 6,656,960 | B2 | 12/2003 | Puskas |
| 6,671,562 | B2 | 12/2003 | Osypka et al. |
| 6,704,604 | B2 | 3/2004 | Soukup et al. |
| 6,760,626 | B1 | 7/2004 | Boveja |
| 6,766,203 | B2 | 7/2004 | Doan et al. |
| 6,778,854 | B2 | 8/2004 | Puskas |
| RE38,654 | E | 11/2004 | Hill et al. |
| RE38,705 | E | 2/2005 | Hill et al. |
| 6,882,887 | B1 | 4/2005 | Shelchuk et al. |
| 6,889,092 | B2 | 5/2005 | Zhu et al. |
| 6,901,297 | B2 | 5/2005 | Frericks et al. |
| 6,934,583 | B2 | 8/2005 | Weinberg et al. |
| 6,934,589 | B2 | 8/2005 | Sundquist et al. |
| 6,973,340 | B2 | 12/2005 | Fuimaono et al. |
| 7,047,084 | B2 | 5/2006 | Erickson et al. |
| 7,058,454 | B1 | 6/2006 | Chitre et al. |
| 7,215,896 | B2 | 5/2007 | Yamada et al. |
| 7,676,275 | B1 | 3/2010 | Farazi et al. |
| 7,917,230 | B2 | 3/2011 | Bly |
| 7,949,409 | B2 | 5/2011 | Bly et al. |
| 8,244,378 | B2 | 8/2012 | Bly et al. |
| 2002/0026228 | A1 | 2/2002 | Schauerte |
| 2002/0029030 | A1 | 3/2002 | Lurie et al. |
| 2002/0032963 | A1 | 3/2002 | Lindegren |
| 2002/0087192 | A1 | 7/2002 | Barrett et al. |
| 2002/0151949 | A1 | 10/2002 | Dahl et al. |
| 2002/0183237 | A1 | 12/2002 | Puskas |
| 2002/0183817 | A1 | 12/2002 | Van Venrooij et al. |
| 2002/0198570 | A1 | 12/2002 | Puskas |
| 2002/0198571 | A1 | 12/2002 | Puskas |
| 2003/0074039 | A1 | 4/2003 | Puskas |
| 2003/0078623 | A1 | 4/2003 | Weinberg et al. |
| 2003/0105506 | A1 | 6/2003 | Krishnan et al. |
| 2003/0195506 | A1 | 10/2003 | Stewart et al. |
| 2003/0195603 | A1 | 10/2003 | Scheiner et al. |
| 2003/0199961 | A1 | 10/2003 | Bjorklund et al. |
| 2003/0229380 | A1 | 12/2003 | Adams et al. |
| 2004/0015151 | A1 | 1/2004 | Chambers |
| 2004/0015204 | A1 | 1/2004 | Whitehurst et al. |
| 2004/0015205 | A1 | 1/2004 | Whitehurst et al. |
| 2004/0019359 | A1 | 1/2004 | Worley et al. |
| 2004/0019377 | A1 | 1/2004 | Taylor et al. |
| 2004/0030362 | A1 | 2/2004 | Hill et al. |
| 2004/0059383 | A1 | 3/2004 | Puskas |
| 2004/0059404 | A1 | 3/2004 | Bjorklund et al. |
| 2004/0062852 | A1 | 4/2004 | Schroeder et al. |
| 2004/0133240 | A1 | 7/2004 | Adams et al. |
| 2004/0147825 | A1 | 7/2004 | Milojevic et al. |
| 2004/0172075 | A1 | 9/2004 | Shafer et al. |
| 2004/0172088 | A1 | 9/2004 | Knudson et al. |
| 2004/0172116 | A1 | 9/2004 | Seifert et al. |
| 2004/0176782 | A1 | 9/2004 | Hanse et al. |
| 2004/0186531 | A1 | 9/2004 | Jahns et al. |
| 2004/0260374 | A1 | 12/2004 | Zhang et al. |
| 2005/0021119 | A1 | 1/2005 | Sage et al. |
| 2005/0038489 | A1 | 2/2005 | Grill |
| 2005/0060014 | A1 | 3/2005 | Swoyer et al. |
| 2005/0060015 | A1 | 3/2005 | Tanaka |
| 2005/0065553 | A1 | 3/2005 | Ezra et al. |
| 2005/0080472 | A1 | 4/2005 | Atkinson et al. |
| 2005/0113862 | A1 | 5/2005 | Besselink et al. |
| 2005/0131467 | A1 | 6/2005 | Boveja |
| 2005/0143412 | A1 | 6/2005 | Puskas |
| 2005/0149126 | A1 | 7/2005 | Libbus |
| 2005/0149155 | A1 | 7/2005 | Scheiner et al. |
| 2005/0149156 | A1 | 7/2005 | Libbus et al. |
| 2005/0197675 | A1 | 9/2005 | David et al. |
| 2005/0251239 | A1 | 11/2005 | Wallace et al. |
| 2006/0009830 | A1 | 1/2006 | Atkinson et al. |
| 2006/0206153 | A1 | 9/2006 | Libbus et al. |
| 2006/0229677 | A1 | 10/2006 | Moffitt et al. |
| 2006/0241737 | A1 | 10/2006 | Tockman et al. |
| 2006/0259085 | A1 | 11/2006 | Zhang et al. |
| 2006/0259107 | A1 | 11/2006 | Caparso et al. |
| 2006/0293741 | A1 | 12/2006 | Johnson et al. |
| 2007/0167955 | A1 * | 7/2007 | Arnault De La Menardiere et al. .............. 606/108 |
| 2008/0051861 | A1 | 2/2008 | Cross et al. |
| 2008/0147168 | A1 | 6/2008 | Ransbury et al. |
| 2008/0167702 | A1 | 7/2008 | Ransbury et al. |
| 2008/0183186 | A1 | 7/2008 | Bly et al. |
| 2008/0183187 | A1 | 7/2008 | Bly |
| 2008/0183248 | A1 | 7/2008 | Rezai et al. |
| 2008/0183253 | A1 | 7/2008 | Bly |
| 2008/0183254 | A1 | 7/2008 | Bly et al. |
| 2008/0183255 | A1 | 7/2008 | Bly et al. |
| 2008/0183259 | A1 | 7/2008 | Bly et al. |
| 2008/0183264 | A1 | 7/2008 | Bly et al. |
| 2008/0183265 | A1 | 7/2008 | Bly et al. |
| 2009/0171425 | A1 | 7/2009 | Dahlberg |
| 2009/0276025 | A1 | 11/2009 | Burnes et al. |
| 2010/0023088 | A1 | 1/2010 | Stack et al. |
| 2010/0049289 | A1 | 2/2010 | Lund et al. |
| 2011/0152877 | A1 | 6/2011 | Bly |
| 2011/0178530 | A1 | 7/2011 | Bly |
| 2012/0035691 | A1 | 2/2012 | Tockman et al. |

FOREIGN PATENT DOCUMENTS

| | | |
|---|---|---|
| EP | 0453117 | 10/1991 |
| EP | 0453117 A1 | 10/1991 |
| EP | 0795343 | 9/1997 |
| EP | 0795343 A2 | 9/1997 |
| EP | 1208867 | 5/2002 |
| EP | 1208867 B1 | 5/2002 |
| EP | 1304135 | 4/2003 |
| EP | 1304135 A2 | 4/2003 |
| JP | 2005-049701 | 3/1993 |
| JP | 5049701 A | 3/1993 |
| JP | 6210009 A | 8/1994 |
| JP | 9187518 A | 7/1997 |
| JP | 2003503119 A | 1/2003 |
| JP | 2008539011 A | 11/2008 |
| WO | WO 8304181 | 12/1983 |
| WO | WO8304181 A1 | 12/1983 |
| WO | WO 9955412 | 11/1999 |
| WO | WO9955412 A1 | 11/1999 |
| WO | WO 9956817 | 11/1999 |
| WO | WO9956817 A1 | 11/1999 |
| WO | WO 0100273 | 1/2001 |
| WO | WO0100273 A1 | 1/2001 |
| WO | WO0137723 A2 | 5/2001 |
| WO | WO 0218006 | 3/2002 |
| WO | WO0218006 A2 | 3/2002 |
| WO | WO03084433 A2 | 10/2003 |
| WO | WO2005065771 A1 | 7/2005 |

| | | |
|---|---|---|
| WO | WO2006098996 A1 | 3/2006 |
| WO | WO2006110338 A1 | 3/2006 |
| WO | WO 2006098996 | 9/2006 |
| WO | WO 2006110338 | 10/2006 |

OTHER PUBLICATIONS

International Search Report and Written Opinion of international application No. PCT/US2007/086118, mailed May 21, 2008, 14 pages.

International Search Report and Written Opinion of international application No. PCT/US2007/086119, mailed Apr. 3, 2007, 15 pages.

International Search Report and Written Opinion of international application No. PCT/US2007/086120, mailed Apr. 14, 2008, 14 pages.

International Search Report and Written Opinion of international application No. PCT/US2007/086124, mailed Apr. 8, 2008, 14 pages.

International Search Report and Written Opinion of international application No. PCT/US2007/086125, mailed Apr. 9, 2008.

International Search Report and Written Opinion of international application No. PCT/US2007/086127, mailed Apr. 3, 2008, 15 pages.

International Search Report and Written Opinion of international application No. PCT/US2007/086130, mailed Apr. 9, 2008, 15 pages.

International Search Report and Written Opinion of international application No. PCT/US2008/051700, mailed Jun. 25, 2008, 13 pages.

International Search Report issued in PCT/US2011/046635, mailed Oct. 26, 2011, 6 pages.

Li et al., "Vagal Nerve Stimulation Markedly Improves Long-Term Survival After Chronic Heart Failure in Rats," Circulation Journal of the American Heart Association, Dec. 8, 2003, pp. 120-124.

Nabutovsky et al., "Lead Design and Initial Applications of a New Lead for Long-Term Endovascular Vagal Stimulation," Pace, vol. 30, Jan. 2007 Supplement 1, pp. S215-S218.

Tarver et al., "Clinical Experience with a Helical Bipolar Stimulating Lead," PACE, October, Part 111992, pp. 1545-1556, vol. 15, Cyberonics. Inc., Webster, Texas and the Department of Neurosurgery, Baylor College of Medicine.

Thompson GW, Levet JM, Miller SM, Hill MR, Meffert WG, Kolata RJ, Clem MF, Murphy DA, Armour JA. Bradycardia Induced by Intravascular Versus Direct Stimulation of the Vagus Nerve. Ann Thorac Surg. Mar. 1998; 65 (3): 637-42.

Web Site, Guidant Fineline II Sterox and Fineline II Sterox EZ, http://www/guidant.com/productstemplates/cnn/fineline_II_sterox.shtml, Aug. 26, 2004, pp. 1-3.

* cited by examiner

NEUROSTIMULATING LEAD HAVING A STENT-LIKE ANCHOR

CROSS-REFERENCE TO RELATED APPLICATIONS

This application is a continuation of application Ser. No. 11/668,834, entitled NEUROSTIMULATING LEAD HAVING A STENT-LIKE ANCHOR, filed Jan. 30, 2007, which is incorporated herein by reference in its entirety for all purposes.

This application is also related to the following co-pending and co-owned applications: SPIRAL CONFIGURATIONS FOR INTRAVASCULAR LEAD STABILITY, filed on Jan. 30, 2007 and assigned Ser. No. 11/668,926; DUAL SPIRAL LEAD CONFIGURATIONS, filed on Jan. 30, 2007 and assigned Ser. No. 11/668,887; ELECTRODE CONFIGURATIONS FOR TRANSVASCULAR NERVE STIMULATION, filed on Jan. 30, 2007 and assigned Ser. No. 11/668,957; TRANSVASCULAR LEAD WITH PROXIMAL FORCE RELIEF, filed on Jan. 30, 2007 and assigned Ser. No. 11/669,039; METHOD AND APPARATUS FOR DELIVERING A TRANSVASCULAR LEAD, filed on Jan. 30, 2007 and assigned Ser. No. 11/669,042; DIRECT DELIVERY SYSTEM FOR TRANSVASCULAR LEAD, filed on Jan. 30, 2007 and assigned Ser. No. 11/669,047; SIDE PORT LEAD DELIVERY SYSTEM, filed on Jan. 30, 2007 and assigned Ser. No. 11/669,050, all of which are herein incorporated by reference in their entireties.

TECHNICAL FIELD

The present invention relates to medical electrical leads for nerve or muscle stimulation. More specifically, the present invention relates to medical electrical lead anchors for stabilizing leads in an intravascular location adjacent a nerve to be stimulated.

BACKGROUND

A significant amount of research has been directed both to the direct and indirect stimulation of nerves including the left and right vagus nerves, the sympathetic and parasympathetic nerves, the phrenic nerve, the sacral nerve, and the cavernous nerve to treat a wide variety of medical, psychiatric, and neurological disorders or conditions. More recently, stimulation of the vagus nerve has been proposed as a method for treating various heart conditions, including heart failure.

Typically in the past, nerve stimulating electrodes were cuffs placed in direct contact with the nerve to be stimulated. A much less invasive approach is to stimulate the nerve through an adjacent vein using an intravascular lead. A lead including one or more electrodes is inserted into a patient's vasculature and delivered at a site within a vessel adjacent a nerve to be stimulated. However, without any additional means of stabilizing the lead within the vein, the lead can move and/or rotate causing the electrodes to migrate from the stimulation site.

Thus, there is a need in the art for a mechanism to minimize intravascular lead rotation and movement and to allow for consistent and reliable delivery of chronic therapy.

SUMMARY

According to one embodiment of the present invention, a medical electrical lead for stimulating a nerve includes: a conductive lead body having a proximal end adapted to be connected to a pulse generator; a distal portion including at least one electrode adapted to deliver an electrical pulse across a vessel wall; and a lead anchor. The lead anchor is adapted to expand from a collapsed configuration to a preformed, expanded configuration, wherein in the collapsed configuration the distal portion has an effective length substantially equal to the effective length of the collapsed lead anchor. The distal portion is coupled to an exterior of the lead anchor such that in the expanded configuration the lead anchor presses the distal portion of the lead against at least one vessel wall of a vessel in which the lead is deployed, securing and stabilizing the distal portion of the lead within the vessel.

According to another embodiment of the present invention, a medical electrical lead for stimulating a nerve from within an adjacent vessel includes: a proximal end adapted to be connected to a pulse generator; a distal portion including at least one electrode adapted to deliver an electrical pulse across a vessel wall; and a lead anchor adapted to expand from a collapsed configuration to a preformed, expanded configuration. The distal portion is coupled to an exterior of the lead anchor.

According to another embodiment of the present invention, a lead anchor assembly for securing and stabilizing a lead within a vessel includes a lead anchor including at least a first end secured to a lead body and a plurality of integrally formed struts extending from the first end secured to the lead body to a second end. The lead anchor can be formed from a laser cut tube of a superelastic material.

A method of stimulating a nerve from within an adjacent vessel is also described. According to one embodiment of the present invention, the method includes providing a medical electrical lead including a lead anchor assembly. A distal portion of the lead mounted to an exterior of the anchor. The lead anchor includes at least a first end secured to a lead and a plurality of struts extending from the first end to a second end and is adapted to expand from a collapsed configuration to a preformed, expanded configuration such that the distal portion of the lead is pressed up against a wall of the vessel. Additionally, the method includes advancing the lead through a patient's vasculature system to a stimulation site located within the vessel; partially deploying the lead anchor assembly such that at least one electrode is exposed; temporarily stimulating the nerve using the partially deployed lead assembly; and determining an optimal stimulation threshold. The method further includes fully deploying the lead anchor assembly and chronically stimulating the adjacent nerve from a stimulation site located with the vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
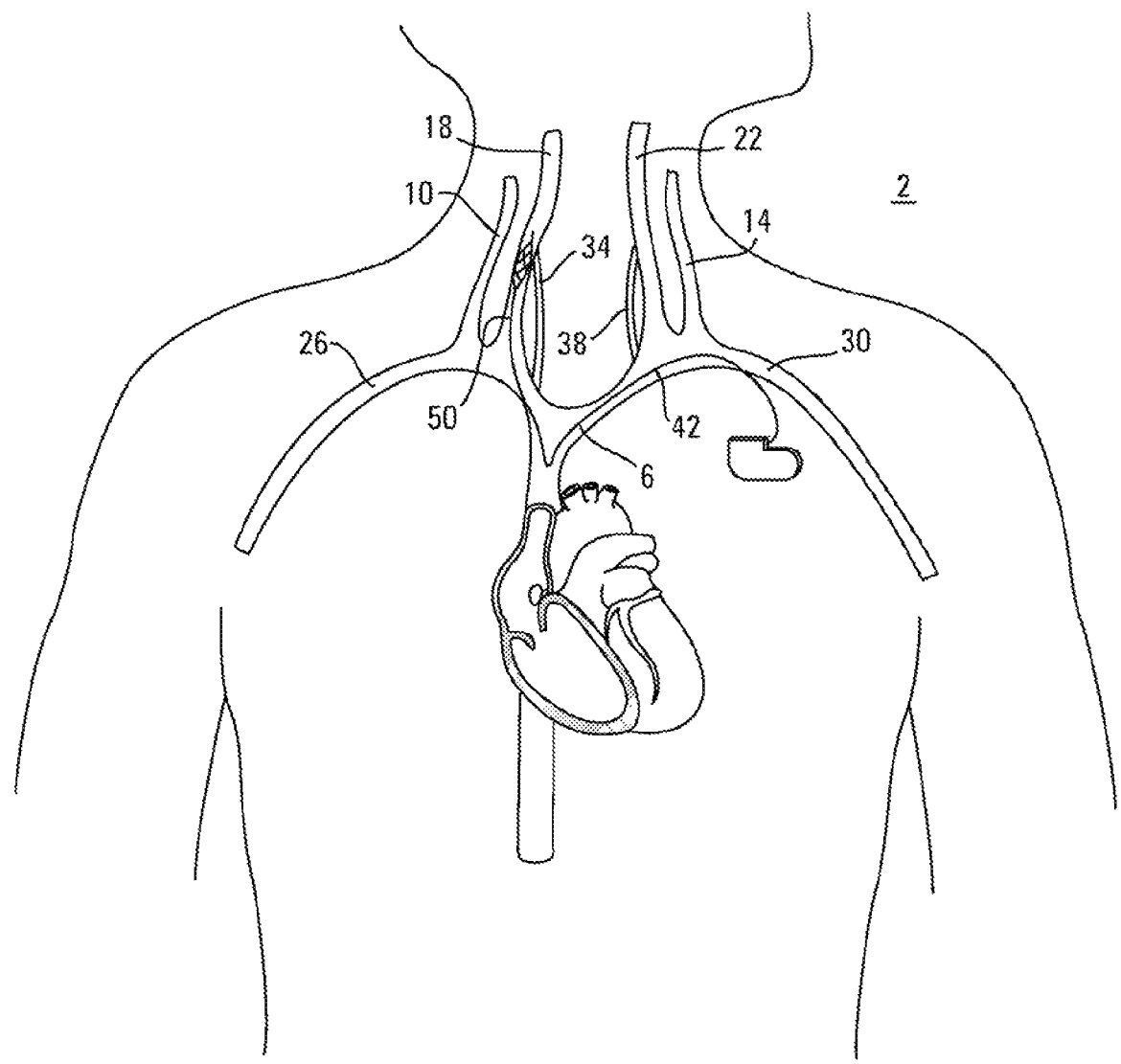
FIGS. 1 and 2 are schematic views of a lead deployed in a patient's internal jugular vein at a location adjacent the vagus nerve according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

While the embodiments described herein generally refer to the placement of a lead into the right internal jugular vein through the right or left subclavian vein, the various embodiments of the present invention as described below can be practiced at numerous sites within a patient's vasculature system. Any intravascular site that is adjacent to a nerve, muscle, or brain tissue that has the potential to benefit from stimulation is a potential site for stimulation. The term "vessel" includes all veins and arteries of the circulatory system. Additionally, the term "vessel" includes various structures of the lymphatic system, including lymph nodes, ducts, capillaries, and vessels. Likewise, as used herein, the term "vessel" also includes the various tube-like structures of the gastrointestinal system. The terms "nerve" and "nerve fiber," as used herein, include a single neuron, nerve, nerve ending(s), or nerve bundle. The term "intravascular" means within a vessel including the veins and arteries of the circulatory system. When referring to "intravascular stimulation" in describing the embodiments of the present invention, it is meant to refer to stimulation from within the circulatory system resulting in (transvascular) stimulation of a nerve, muscle, or tissue of interest. The term "transvascular" means across a vessel or vessel wall. "Stimulation" means a stimulus, usually electrical, which causes depolarization of a cell or cells, or portion of a cell, contraction, excitation as measured by, e.g., calcium or sodium influx into the cell, or an altered membrane potential across a cell.

Vessels having sufficient diameter for catheter access which are known to have nerves running adjacent to or nearby are suitable candidates for potential stimulation sites. Exemplary sites include, but are not limited to, the following: the left and right internal jugular veins, the azygous vein, the brachiocephalic (innominate) vein, the subclavian vein, the superior vena cava, the pulmonary artery, and cardiac branch vessels. Other potential stimulation sites include, but are not limited to, the following: thoracic duct, the bile duct, and sites along the upper gastrointestinal and lower gastrointestinal tracts. Exemplary nerves to be stimulated include, but are not limited to, the following: the left and right vagus nerves, the phrenic nerve, the parasympathetic nerves, the sympathetic nerves, and the sacral nerve.

Figure 2:
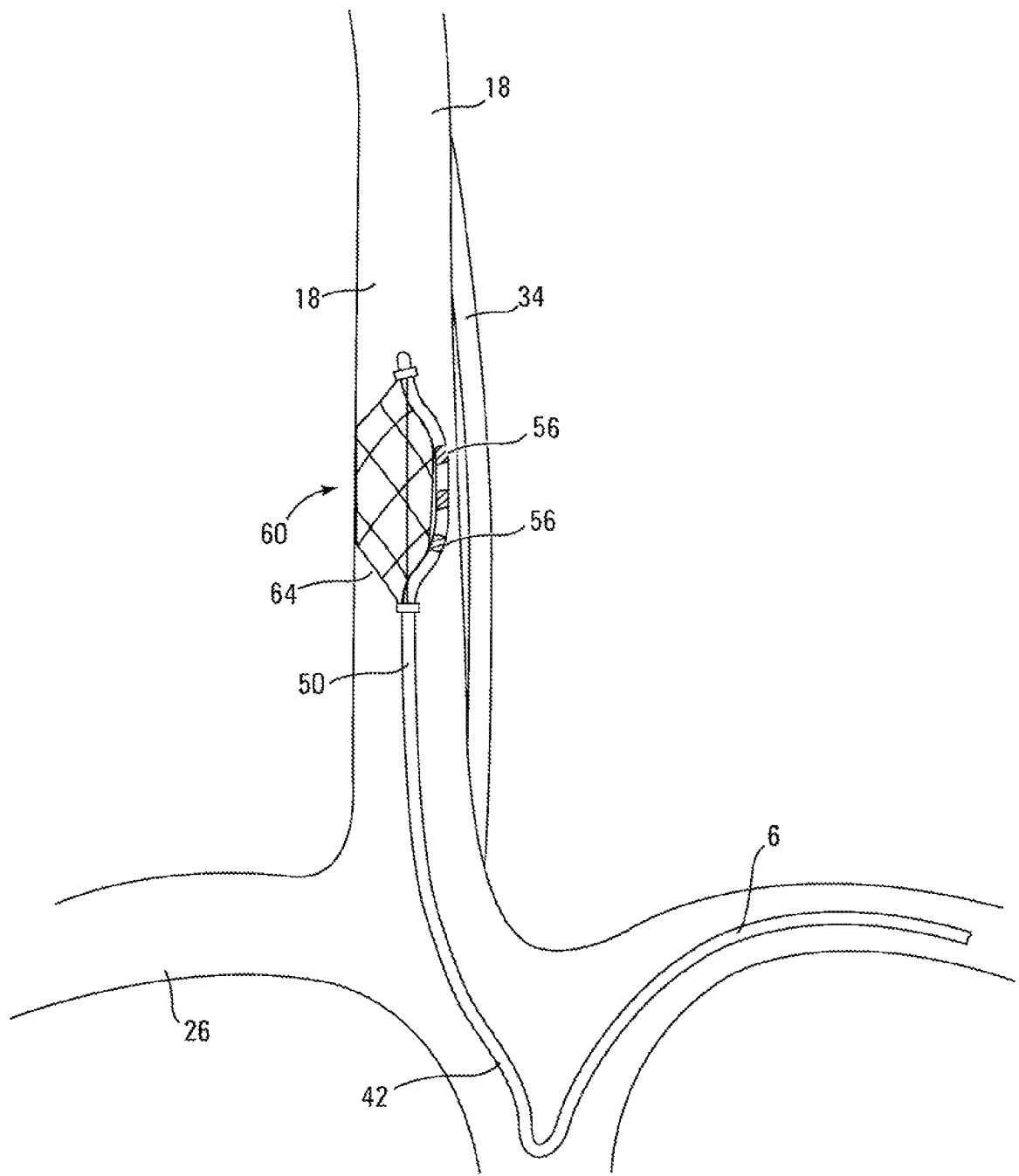

FIG. 1 shows a perspective view of a patient's vascular system 2 including a lead 6 deployed within the system 2. FIG. 2 is a close-up schematic view of the lead 6 deployed within the system 2. In general, the vascular system 2, as shown, includes the right and left external jugular veins 10 and 14, the right and left internal jugular veins 18 and 22, the right and left subclavian veins 26 and 30, portions of which are generally aligned with the right and left vagus nerves 34 and 38. As shown in FIGS. 1 and 2, the lead 6 is inserted into a patient's vasculature system through the left subclavian vein 30 and into the right internal jugular vein 18. The lead 6 is positioned in the right internal jugular vein 18 adjacent to the right vagus nerve 34. Alternatively, the lead 6 can be inserted and advanced to a stimulation site within the right internal jugular vein 18 via the right subclavian vein 26.

The lead 6 includes a lead body 42 including a proximal end and a distal portion 50. One or more electrodes 56 (FIG. 2) are positioned along the lead body 42. In particular, the electrodes 56 are located on the distal portion 50 of the lead 6. The proximal end of the lead is adapted to be connected to a pulse generator or other implantable device. The lead body 42 is flexible, and typically has a circular cross-section.

According to another embodiment of the present invention, the lead body 42 includes a plurality of conductors including individual wires, coils, or cables. The conductors can be insulated and/or molded in place with an insulator such as silicone, polyurethane, ethylene tetrafluoroethylene, or another biocompatible, insulative polymer. In one exemplary embodiment, the lead body 42 has a co-radial design. In this embodiment, each individual conductor is separately insulated and then wound together in parallel to form a single coil. In another exemplary embodiment, the lead body 42 is co-axial. According to a further embodiment of the present invention, each conductor is adapted to connect to an individual electrode 56 in a one-to-one manner allowing each electrode 56 to be individually addressable. In yet a further embodiment of the present invention, the lead body 42 includes a lumen adapted to receive a guiding element such as a guide wire or a stylet.

The lead 6 also includes a distal portion 50. The distal portion 50 can have a similar or different construction than the lead body 42. According to one embodiment, the distal portion 50 of the lead 6 is stiffer than the lead body 42. One exemplary embodiment of such a structure is disclosed in commonly assigned and co-pending application entitled "TRANSVASCULAR LEAD WITH PROXIMAL FORCE RELIEF", assigned Ser. No. 11/669,039, which is herein incorporated by reference. According to another embodiment of the present invention, the distal portion 50 includes a material, which may impart a desired shape useful for anchoring or securing the distal portion 50 of the lead 6 in a vessel. Exemplary materials include Nitinol and other materials known in the art.

The distal portion 50 includes a lead anchor 60. As shown in FIGS. 3A-4C, the distal portion 50 of the lead 6 is mounted to an exterior 64 of the lead anchor 60. The distal portion 50 is mounted to the anchor 60 using a variety of means including adhesives, welding, suturing or otherwise bonding the distal portion 50 to the lead anchor 60.

Figure 3A:
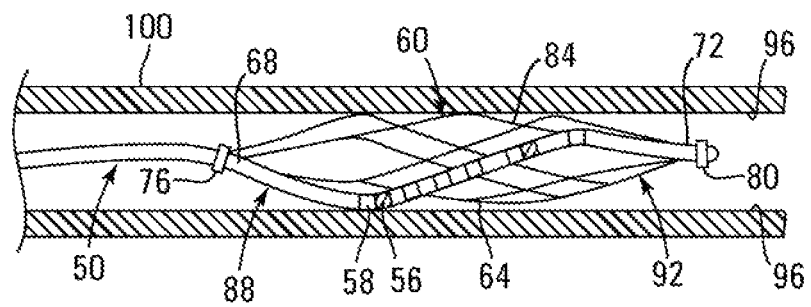
FIGS. 3A-3D are schematic views of a distal portion of a lead including a lead anchor including tapered proximal and distal ends deployed within a vessel according to various embodiments of the present invention.
Figure 3B:
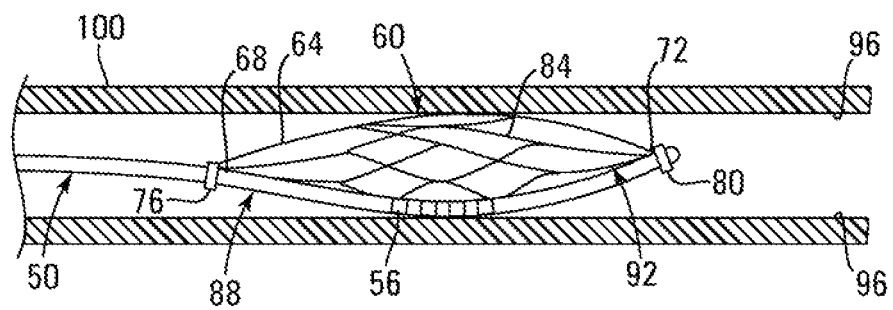
Figure 3C:
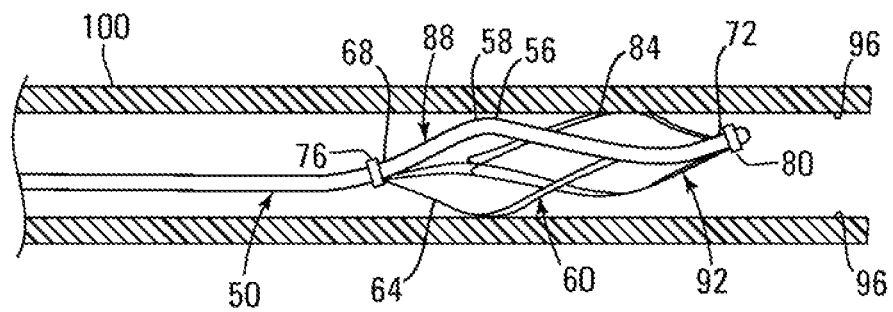
Figure 3D:
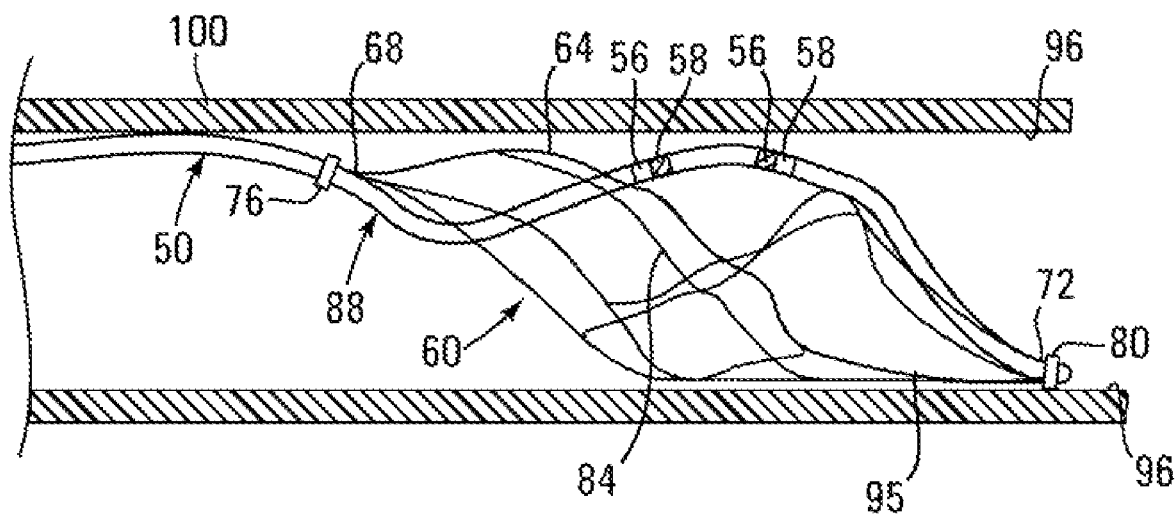

The distal portion 50 can be mounted to the lead anchor 60 such that it follows a curvature of a strut forming the anchor 60, as shown in FIGS. 3A, 3C, 4A, and 4B. Alternatively, the distal portion 50 can be mounted such that it is substantially straight along the length of the anchor 60, as shown in FIGS. 3B and 4C. According to another embodiment of the present invention, the distal portion 50 of the lead 6 is mounted to the exterior 64 of the lead anchor 60 such that a first end 68 of the distal portion 50 of the lead 6 is generally aligned with a second end 72 (shown in FIGS. 3A-3C). More particularly, in these embodiments, the distal portion 50 of the lead is mounted to the exterior 64 such that the first end 68 is radially aligned with the second end 72. Alternatively, the distal portion 50 of the lead 6 is mounted to the exterior 64 of the lead anchor such that the first end 68 of the distal portion 50 of the lead 6 is radially offset from the second 62, for example as shown in FIG. 3D.

According to another exemplary embodiment, the distal portion 50 is bifurcated. The bifurcated distal portion 50 includes a first elongate member and a second elongate member. Each elongate member of the bifurcated distal portion is mounted to an exterior of the lead anchor 60. The elongated members can each follow a curvature of a strut forming the anchor 60. Alternatively, the elongated members can be mounted such that they are substantially straight along the length of the anchor. According to yet another example, an elongated member can follow a curvature of a strut with the other elongate member mounted such that it is substantially straight along the length of the anchor 60.

According to another exemplary embodiment of the present invention, the distal portion 50 can include one or more recesses in an outer layer of the lead body 42. The recesses are adapted to receive a portion or the entire lead anchor 60. The recesses enable the distal portion 50 to maintain a lower profile on the lead anchor 60 as well as providing for a more secure mounting.

The distal portion 50 also includes one or more electrodes 56. The electrodes 56 can have any configuration as is known in the art. Exemplary electrode configurations can be found in the commonly assigned and co-pending application entitled "ELECTRODE CONFIGURATIONS FOR TRANSVASCULAR NERVE STIMULATION," assigned Ser. No. 11/668,957, which is herein incorporated by reference. In various exemplary embodiments of the present invention, the electrodes 56 can be ring or partial ring electrodes and can include a drug-eluting collar 58 adjacent the electrode 56. At least one electrode 56 is adapted to deliver an electrical pulse transvascularly to the nerve or muscle to be stimulated. According to one embodiment of the present invention, the distal portion 50 includes multiple electrodes 56 spaced an equal distance from one another along the distal portion 50. The electrodes 56 can have the same or differing polarities. Additionally, the electrodes 56 can be connected to multiple individual conductors through the lead body 42 allowing for them to be individually addressable. Individually addressable electrodes 56 allow for flexibility in electrode selection providing for greater control over the current field and the direction of stimulation as well as allowing for multiple options for stimulation and sensing.

According to one exemplary embodiment of the present invention, the lead anchor 60 is made from a superelastic material. Exemplary superelastic materials includes Nitinol, MP35N, and other materials well-known in the art. According to one embodiment of the present invention, the lead anchor 60 is formed from a laser-cut Nitinol tube using techniques generally known in the art. The Nitinol tube is cut with a laser to remove material leaving behind at least one collar having a diameter equal to that of the original tube diameter and one or more integrally-formed, expandable struts. The struts can be connected forming one or more cells. Additionally, the struts can have a braided or non-braided configuration. According to an alternate embodiment of the present invention, the lead anchor 60 can be formed from one or more superelastic wires. Like the integrally formed struts, the wires can be connected to form one or more cells. As the number of cells increase, the anchor can take on a cage or basket like appearance. Additionally, the wires can have a braided or non-braided configuration. Finally, the wires can be spiraled, canted or arced and can have various configurations adapted to minimize the amount of strain on the wires.

According to one embodiment of the present invention, the lead anchor 60 includes at least one collar 76 secured to an end of the distal portion of the lead 6. As shown in FIGS. 3A-3D, the lead anchor 60 includes a proximal collar 76 secured to the first end 68 of the distal portion 50 of the lead 6 and a distal collar 80 secured to the second end 72. At least one expandable strut 84 extends from the proximal collar 76 to the distal collar 80. The expandable strut 84 is formed such that it is adapted to bias the distal portion 50 including the electrodes against a vessel wall of a vessel in which the distal portion 50 is deployed. According to another embodiment of the present invention, the lead anchor 60 includes a plurality of expandable struts 84 extending from the proximal collar 76 to the distal collar 80. According to a further embodiment of the present invention, as shown in FIGS. 3A-3D, the expandable struts 84 forming the lead anchor 60 include a proximal tapered region 88 connected to the proximal collar 76 and a distal tapered region 92 connected to the distal collar 80. The tapered regions 88 and 92 aid in the delivery and the retraction of the distal portion 50 of the lead 6.

Figure 4A:
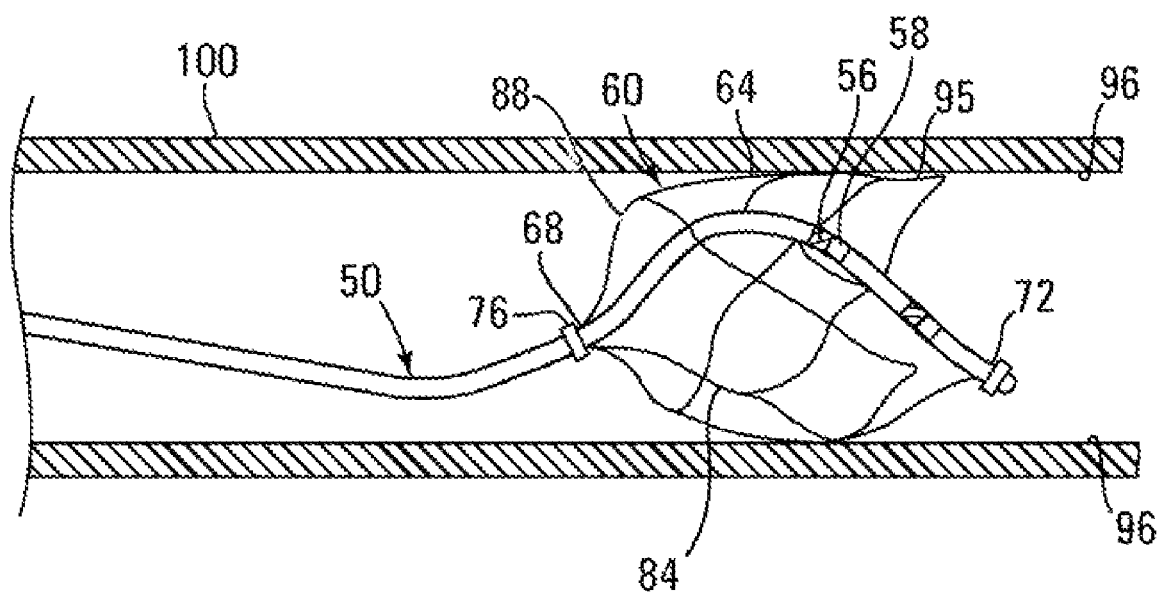
FIGS. 4A-4C are schematic views of a distal portion of a lead including a lead anchor having a single tapered end deployed within a vessel according to various embodiments of the present invention.
Figure 4B:
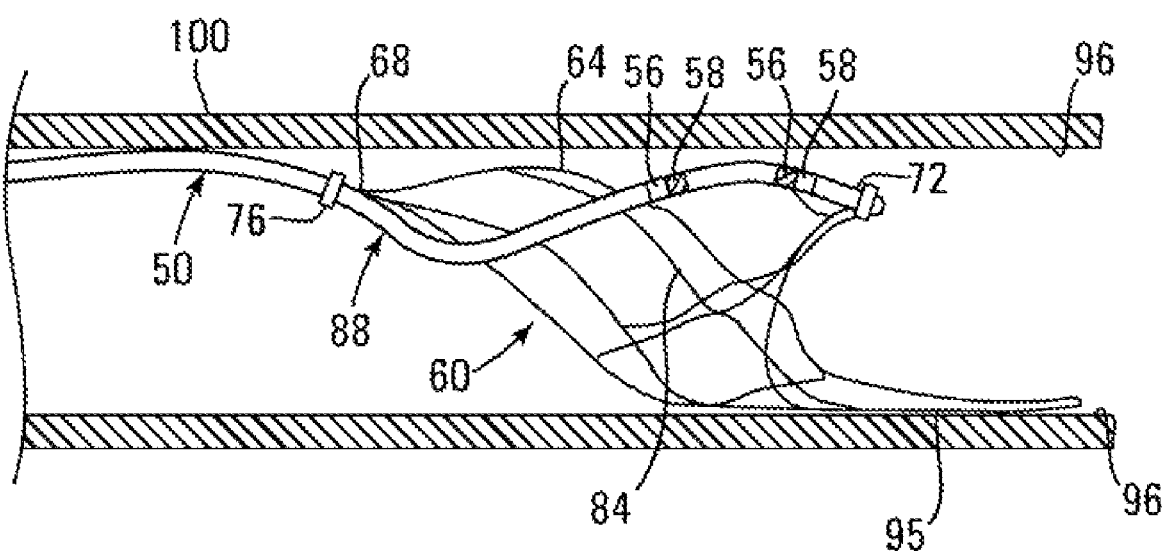
Figure 4C:
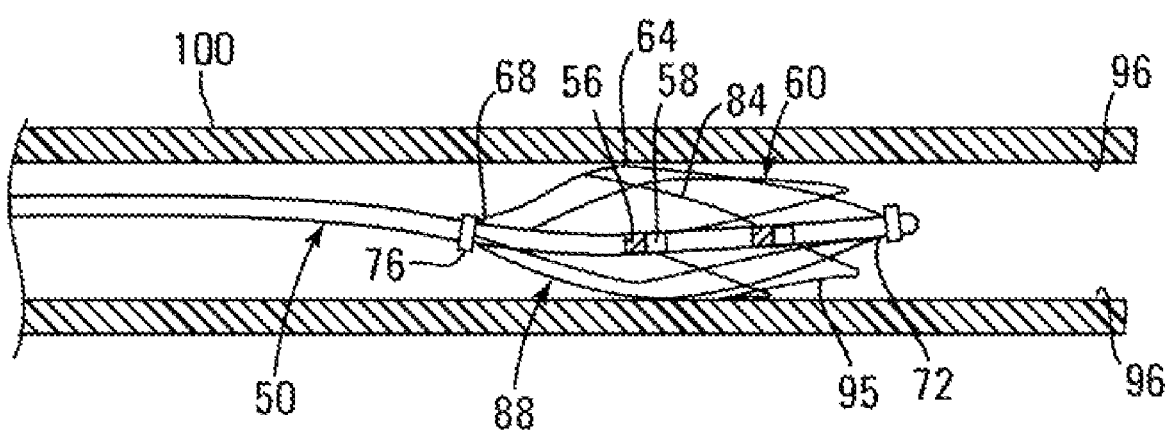

According to alternative embodiments of the present invention, as shown in FIGS. 4A-4C, the lead anchor 60 includes a single proximal collar 76 attached to the first end 68 of the distal portion 50. As shown in FIGS. 4A-4C, the lead anchor 60 includes a plurality of expandable struts 84 extending from the proximal collar 76 towards a distal end 72 of the distal portion 50. The expandable struts 84 include a tapered proximal region 88 connected at one end to the collar 76. The distal end 95 of the lead anchor 60 does not include a collar and thus the anchor 60 remains open-ended at its distal end 95.

According to a further embodiment of the present invention, the lead anchor 60 includes a biocompatible coating. According to various embodiments, the coating includes polyurethane, silicone, EFTE, PTFE, or another biocompatible material as is known in the art. According to another embodiment of the invention, the struts 84 can be individually coated with a biocompatible coating. According to yet a further embodiment of the present invention, a polymer sleeve covering the stent-like anchor 60 also can be utilized.

According to a further embodiment of the present invention, as shown in FIGS. 3A-4C, the lead anchor 60 is adapted to expand from a collapsed configuration to an expanded configuration. In the expanded configuration, the lead anchor 60 presses the distal portion 50 of the lead 6 and its electrodes 56 up against a vessel wall 96 of a vessel 100 in which the distal portion 50 of the lead 6 is deployed. The lead anchor 60 expands with sufficient radial force as to effectively minimize rotation and migration of the distal portion 50 including its electrodes 56 away from the target stimulation site, thus securing and stabilizing the distal portion 50 of the lead 6 within the vessel 100. Force is distributed along the expanded length of the anchor 60 providing for a more effective and stable anchoring mechanism. According to an embodiment of the present invention, the lead anchor 60 places enough radial expansion force on the vessel walls such that the distal portion 50 migrates outside of the original boundaries of the vessel walls 96 and towards the nerve to be stimulated without damaging the vessel walls 96. As a result, any electrodes 56 located on the distal portion 50 are placed in closer proximity to the nerve. According to one exemplary embodiment of the present invention, the distance between the electrodes 56 and the nerve 34 to be stimulated is about less than 2 mm.

The migration of the distal portion 50 outside of the original boundaries of the vessel walls 96 causes no damage to the vessel walls 96 nor does the spiral erode through the vessel walls 96. A sheath of tissue forms over the distal portion 50 over an extended period of time such that it becomes encapsulated within the vessel walls 96. The outer geometry of the vessel 100 is altered such that the outline of the distal portion 50 of the lead 6 located within the vessel 100 is visible.

When expanded, a length of the lead anchor 60 ranges from about 6 to about 120 mm. Additionally, according to one embodiment of the present invention, an effective outer diameter of the expanded lead anchor 60 ranges from about 3 to about 40 mm. According to another embodiment of the present invention, the expanded lead anchor 60 has an effective outer diameter ranging from about 10 to about 25 mm. The size of the lead anchor 60 is selected such that, when in the expanded configuration, the lead anchor 60 has an outer diameter slightly larger than the inner diameter of the vessel 100 in which it is to be deployed. According to one exemplary embodiment, the outer diameter of the lead anchor 60 ranges from about 5 percent to 40 percent greater than the inner diameter of the vessel 100 in which the distal portion 50 is deployed. According to a further embodiment, the lead anchor 60 can be sized such that it can be used in conjunction with a lead adapted to be delivered to the left side of the heart as well as other locations within a patient's vasculature system.

Figure 5A:
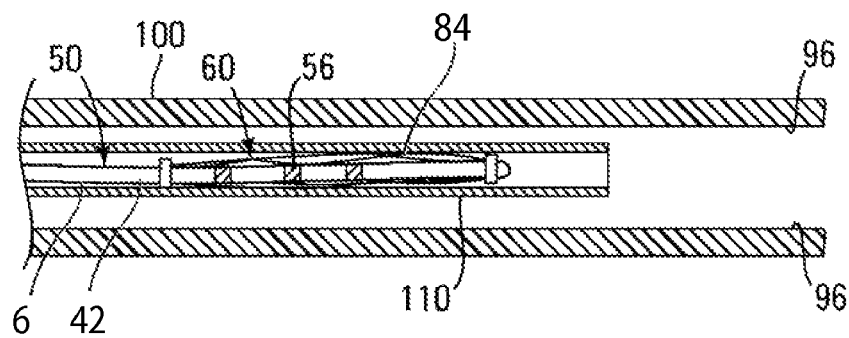
FIGS. 5A-5C are partial cross-sectional views of a lead including a lead anchor during delivery and deployment within a vessel according to an embodiment of the present invention.
Figure 5B:
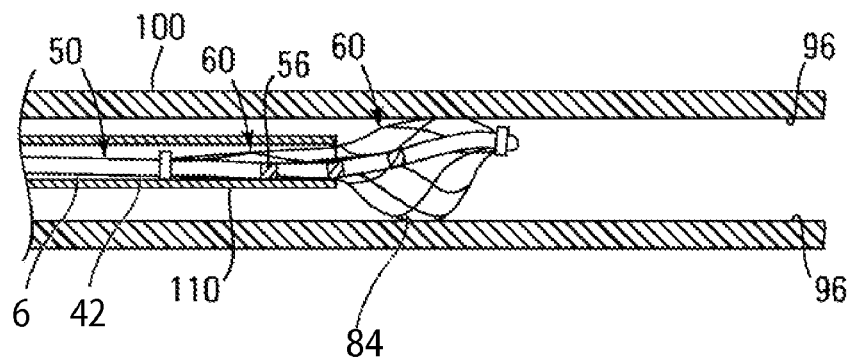
Figure 5C:
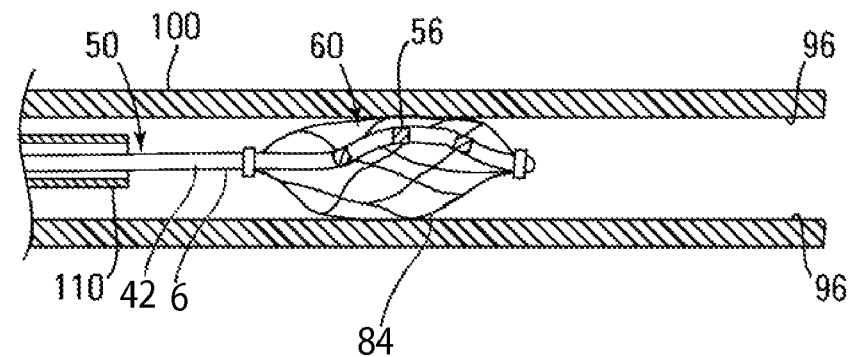

FIGS. 5A-5C show a distal portion 50 of the lead 6 during delivery and deployment within a vessel 100. In the collapsed configuration, as shown in FIG. 5A, the effective length of the distal portion 50 is substantially equal to the effective length of the lead anchor 60. According to one embodiment of the present invention, the collapsed lead anchor 60 including the distal portion 50 mounted thereto has an outer diameter ranging from about 1 to about 4 mm. According to one exemplary embodiment of the present invention, the collapsed lead anchor 60 has an overall length ranging from about 6 to about 200 mm. According to another embodiment of the present invention, the collapsed lead anchor has an overall length ranging from about 10 to about 80 mm.

According to one exemplary embodiment of the present invention, as shown in FIGS. 5A-5C, the lead anchor 60 is adapted to be retained within a guide catheter 110 or other suitable member capable of retaining the lead anchor 60 in its collapsed configuration for insertion and delivery within a patient's vasculature system, including any suitable vessel that is adjacent a nerve to be stimulated. According to another embodiment of the present invention, the lead body 42 can include a lumen adapted to receive a guiding element such as a stylet or a guide wire adapted to assist in the delivery of the distal portion 50 including the lead anchor 60 to a stimulation site within a vessel. According to these embodiments, a stylet, guide wire, or guide catheter 110, either alone or in combination with one another, is used to collapse (either fully or partially) the distal portion 50 including the lead anchor 60 from an expanded configuration to a collapsed configuration (full or partial) and also to guide the distal portion 50 of the lead 6 through the patient's vasculature system to a stimulation site located within a vessel 100. In the collapsed configuration, as shown in FIG. 5A, the lead anchor 60 including the distal portion 50 mounted thereto can be inserted into a patient's vasculature system and guided to a stimulation site within a vessel 100.

According to a further embodiment of the present invention, as shown in FIGS. 5A-5C, a guide catheter 110 is used to deliver the lead anchor 60 including the distal portion 50 mounted thereto to the stimulation site within a vessel. Once inside the targeted vessel, as shown in FIG. 5B, the lead anchor 60 including the distal portion 50 can be partially deployed from the guide catheter 110 and rotated or otherwise manipulated. The electrodes 56 located on the distal portion 50 can be used to acutely stimulate and, thus, test potential stimulation sites. Once a stimulation site has been selected using the information gained through acute stimulation, the guide catheter 110 can be retracted and the lead anchor 60 fully deployed, as shown in FIG. 5C, so as to secure and stabilize the distal portion 50 of the lead 6 at a stimulation site within the vessel 100 such that transvascular stimulation of the adjacent nerve or muscle can occur.

According to yet another embodiment of the present invention, the lead anchor 60 is variably expandable. That is, the lead anchor 60 is adapted to expand with and adapt to the natural changes in the size and diameter of the vessel 100 while at the same time engaging and maintaining a frictional force on the vessel walls 96. For example, when in the internal jugular vein 18, 22 (FIG. 2), the internal geometry (diameter and inner shape) of the internal jugular vein 18, 22 may change with blood flow and blood pressure. Similarly, when a patient is in an upright position, the diameter of the vessel 100 may be smaller than when the patient is lying down or is in a prone position. The lead anchor 60 accounts for the difference in vessel diameter by expanding so as to maintain a frictional force on the vessel walls 96 securing and stabilizing the distal portion 50 in the vessel.

The distal portion 50 of the lead 6, according to various embodiments of the present invention, can be delivered to a stimulation site within a vessel adjacent a nerve, muscle, or tissue to be stimulated using standard techniques. According to one embodiment of the present invention, the lead 6 can be inserted in a patient's vasculature system via a percutaneous stick directly into a patient's internal jugular vein to deliver therapy to the vagus nerve. According to another embodiment of the present invention, the lead anchor 60, to which the distal portion 50 is mounted, is transitioned to a collapsed configuration and advanced through a patient's vasculature system and delivered to a stimulation site using a guiding element such as a guide catheter. Once the site has been reached and the guide catheter is retracted, the lead anchor 60 is allowed to transition from its collapsed configuration to its expanded configuration, contacting and frictionally engaging the vessel walls of the vessel in which it is deployed. Likewise, a stylet or one or more guide wires may be inserted into a lumen located within the lead body 42 to transition the lead anchor 60 to transition from its predetermine expanded shape to a collapsed configuration. The distal portion 50 is then guided through the vasculature to a stimulation site located within a vessel. Once a stimulation site has been reached, the guide wire or stylet is removed allowing the lead anchor 60 to return to its predetermined shape. Pull wires can also be used to further expand the lead anchor 60 within a vessel such that the expandable struts 84 forming the anchor 60 place an additional radial force on the wall further securing and stabilizing the lead 6 within the vessel.

Whatever the delivery method, once the lead anchor 60 including the distal portion 50 mounted thereto has reached a stimulation site within a vessel 100 adjacent a nerve to be stimulated, the lead anchor 60 expands forcing the distal portion 50 mounted to an exterior of the lead anchor 60 to contact and frictionally engage the vessel walls 96 of the vessel 100 in which the distal portion 50 including the lead anchor 60 is deployed. The lead body 42 and, thus, the lead anchor 60 can be rotated within the vessel 100 to orient the electrodes 56 towards the stimulation target. Additionally, the lead body 42 can be further rotated or positioned until a maximum or optimum electrical stimulation threshold by the electrodes 56 has been achieved across the vessel wall 96 to the adjacent nerve or muscle to be stimulated. The stimulating pulse delivered by the electrodes 56 can then be measured to determine if an optimal stimulation threshold has been reached.

The distal portion 50 can be repositioned within the vessel by either rotating the lead body 42 within the vessel or reintroducing the guiding member such as the guide catheter 110 or guide wire to collapse (partially or fully) the lead anchor 60. The distal portion 50 mounted to an exterior of the lead anchor 60 can be then either repositioned and/or removed from the vessel 100. According to a further embodiment of the present invention, the distal portion 50 can be partially deployed from a guide catheter 110 in order to acutely stimulate the nerve. Once a suitable stimulation site has been identified using acute stimulation, the guide catheter 110 can be retracted and the lead anchor 60 including the distal portion 50 mounted to its exterior can be fully deployed within the vessel 100 at the stimulation site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A method of deploying an implantable medical electrical lead for stimulating a nerve from within an adjacent vessel, the method comprising: collapsing an expandable lead anchor having a first end coupled to a distal portion of a medical electrical lead body at a first location and a second end coupled to the distal portion of the lead body at a second location distal to the first location into a radially collapsed configuration, wherein the distal portion of the lead body includes a plurality of conductors extending within the lead body from a proximal end thereof toward a distal end thereof, with each conductor being coupled to one of a plurality of individual ring electrodes, the plurality of individual ring electrodes longitudinally spaced along a length of the distal portion of the lead body and located thereon between the first and the second locations, each of the plurality of individual ring electrodes being adapted to transvascularly deliver an electrical pulse to a nerve to be stimulated, the distal portion extending along and contacting an exterior of the expandable lead anchor; guiding the collapsed lead anchor coupled to the distal portion of the lead body to a location within a vessel adjacent the nerve to be stimulated; and causing or allowing the expandable lead anchor to expand from the radially collapsed configuration to a radially expanded configuration to urge the distal portion of the lead body including the plurality of individual ring electrodes located thereon into contact with a wall of the vessel in which the lead is delivered so as to secure and stabilize the distal portion of the lead body in the vessel.

2. The method according to claim 1, further comprising rotating the lead anchor to orient the plurality of individual ring electrodes located on the distal portion of the lead body in a direction towards the nerve to be stimulated.

3. The method according to claim 1, wherein causing or allowing the expandable lead anchor to assume the radially expanded configuration includes partially expanding the lead anchor from the radially collapsed configuration to a partially expanded configuration followed by rotating the partially expanded lead anchor.

4. The method according to claim 1, wherein collapsing the expandable lead anchor includes retaining the expandable lead anchor coupled to the distal portion of the lead body within a guide catheter, wherein the guide catheter is adapted to retain the lead anchor coupled to the distal portion of the lead body in the radially collapsed configuration.

5. The method according to claim 1, wherein collapsing the expandable lead anchor includes inserting an elongated member into a lumen provided within the lead body to collapse the expandable lead anchor from the radially expanded configuration to the radially collapsed configuration.

6. The method according to claim 1, wherein expanding the expandable lead anchor includes retracting a guide catheter used to collapse and retain the expandable anchor in the radially collapsed configuration.

7. The method according to claim 1, wherein causing or allowing the expandable lead anchor to assume the radially expanded configuration includes withdrawing an elongated member from a lumen provided within the lead body, the elongated member used to collapse and retain the expandable anchor in the radially collapsed configuration.

8. The method according to claim 1, further comprising acutely testing potential stimulation sites using the plurality of individual ring electrodes located on the distal portion of the lead body.

9. The method according to claim 8, further comprising selecting a stimulation site using information from acutely testing potential stimulation sites.

10. The method according to claim 1, further comprising repositioning the lead after causing or allowing the expandable lead anchor to assume the radially expanded configuration.

11. The method according to claim 10, wherein repositioning the lead includes at least partially collapsing the expandable lead anchor from the radially expanded configuration.

12. The method according to claim 1, wherein the vessel is the superior vena cava.

13. The method according to claim 1, wherein the vessel is the brachiocephalic vein.

14. The method according to claim 1, wherein the vessel is the internal jugular vein and the nerve is the vagus nerve.

15. A method of deploying an intravascular lead for stimulating a nerve from within an adjacent vessel, the method comprising; delivering the intravascular lead to a location within the vessel adjacent the nerve to be stimulated, the intravascular lead including a lead body comprising a distal portion including a plurality of individual ring electrodes located thereon, wherein the plurality of individual ring electrodes are longitudinally spaced along a length of the distal portion of the lead body, and a plurality of conductors extending within the lead body from a proximal end thereof toward a distal end thereof, with each conductor being coupled to one of the individual ring electrodes, the distal portion of the lead body extending along and coupled to an exterior of an expandable lead anchor, wherein the expandable lead anchor has a first end coupled to a distal portion of the intravascular lead at a first location and a second end coupled to the distal portion of the intravascular lead at a second location distal to the first location, and the expandable lead anchor is adapted to expand from a radially collapsed configuration to a radially expanded configuration, wherein the expandable lead anchor is retained within the radially collapsed configuration during delivery of the lead; partially transitioning the expandable lead anchor from the radially collapsed configuration to a partially expanded configuration wherein at least one of the plurality of individual ring electrodes located on the distal portion of the lead body coupled to the expandable lead anchor is exposed within the vessel; acutely stimulating the nerve; and transitioning the expandable lead anchor from the partially expanded configuration to the radially expanded configuration to urge the distal portion of the lead body including the plurality of individual ring electrodes into contact with a vessel wall of the vessel in which the lead is deployed so as to secure and stabilize the distal portion of the lead body within the vessel.

16. The method according to claim 15, further comprising rotating the partially expanded lead anchor to orient at least one of the plurality of individual ring electrodes located on the distal portion of the lead body in a direction toward the nerve to be stimulated.

17. The method according to claim 15, wherein delivering the intravascular lead to the location within the vessel adjacent a nerve to be stimulated includes using a guide catheter to advance the lead to the location within the vessel, wherein the guide catheter is adapted to retain the lead anchor including the distal portion of the lead body in the radially collapsed configuration for delivery.

18. The method according to claim 15, wherein delivering the intravascular lead to the location within the vessel adjacent a nerve to be stimulated includes using an elongated member inserted into a lumen extending within the lead body to advance the lead to the location within the vessel, wherein the elongated member is adapted to retain the lead anchor including the distal portion of the lead body in the radially collapsed configuration for delivery.

19. The method according to claim 15, further comprising determining an optimal stimulation threshold after acutely stimulating the nerve.

20. The method according to claim 15, further comprising partially collapsing the expandable lead anchor and repositioning the lead.

* * * * *